United States Patent [19]

Hendrix

[11] Patent Number: 5,464,741
[45] Date of Patent: Nov. 7, 1995

[54] PALLADIUM (II) OCTAETHYLPORPHINE ALPHA-ISOTHIOCYANATE AS A PHOSPHORESCENT LABEL FOR IMMUNOASSAYS

[75] Inventor: John L. Hendrix, Palm Harbor, Fla.

[73] Assignee: Henwell, Inc., Palm Harbor, Fla.

[21] Appl. No.: 134,133

[22] Filed: Oct. 8, 1993

[51] Int. Cl.$^6$ ........................................ C12Q 1/70
[52] U.S. Cl. ................. 435/5; 435/6; 435/7.1; 435/7.2; 435/7.3; 435/7.4; 435/7.5; 435/7.6; 435/968; 436/546; 436/548; 436/816; 436/817; 436/818; 540/145
[58] Field of Search ................. 435/5, 6, 7, 7.6, 435/968; 540/145; 424/1.1, 85.8, 88, 89, 1.49; 436/546, 548, 816–818

[56] References Cited

U.S. PATENT DOCUMENTS

| | | | |
|---|---|---|---|
| 4,058,732 | 11/1977 | Wieder | 250/461 B |
| 4,234,455 | 11/1980 | Homeier | 252/430 |
| 4,578,491 | 3/1986 | Amundsen | 556/137 |
| 4,614,723 | 9/1986 | Schmidt et al. | 436/536 |
| 4,622,174 | 11/1986 | McKoy | 252/582 |
| 4,659,676 | 1/1987 | Rhyne | 436/56 |
| 4,751,068 | 6/1988 | Bickar | 423/437 |
| 4,783,529 | 11/1988 | Lavallee et al. | 540/145 |
| 4,863,875 | 9/1989 | Bailey | 436/518 |
| 4,885,114 | 12/1989 | Gordon | 252/589 |
| 4,898,985 | 2/1990 | Ito et al. | 568/344 |
| 4,935,166 | 6/1990 | Lee | 252/582 |
| 5,082,642 | 1/1992 | Bickar | 423/402 |
| 5,102,213 | 4/1992 | Lee | 359/890 |
| 5,102,625 | 4/1992 | Milo | 422/82.07 |
| 5,120,882 | 7/1992 | Ellis, Jr. | 568/910 |
| 5,120,886 | 7/1992 | Lyons | 568/909.8 |
| 5,155,149 | 10/1992 | Atwater | 524/88 |
| 5,156,840 | 10/1992 | Goers et al. | 424/85.91 |
| 5,158,922 | 10/1992 | Hinney et al. | 502/175 |
| 5,162,231 | 11/1992 | Cole et al. | 436/64 |
| 5,268,371 | 12/1993 | Mauclaire et al. | 514/185 |

FOREIGN PATENT DOCUMENTS

| | | | |
|---|---|---|---|
| 2171656 | 12/1988 | Japan | 436/546 |
| 2086042 | 5/1982 | United Kingdom | 436/545 |
| 8002076 | 10/1980 | WIPO . | |

OTHER PUBLICATIONS

Biological Abstract 88(7):74113, Savitskii et al, "Phosphorescence immunoassay: Metalloporphyrins as an Alternative of rare earth fluorescent labels", abstract published 01 Oct. 1989.
Tietz (ed), Textbook of Clinical Chemistry, (W. B. Sanders Company 1986) pp. 64 and 1590.

*Primary Examiner*—Carol A. Spiegel
*Attorney, Agent, or Firm*—Joseph C. Mason, Jr.; Ronald E. Smith; Louise A. Foutch

[57] ABSTRACT

A phosphorescence assay system. The phosphorescent label for immunoassays is palladium (II) octaethylporphine alphaisothiocyanate. The labeling agent has a Stokes shift of not less than 150 nanometers. Method for preparing the palladium (II) phosphorescent label is also shown.

7 Claims, 1 Drawing Sheet

PALLADIUM (II) OCTAETHYLPORPHINE ALPHA-ISOTHIOCYANATE AS A PHOSPHORESCENT LABEL FOR IMMUNOASSAYS

BACKGROUND OF THE INVENTION

1. Field of the Invention

The present invention relates to a novel phosphorescent compound and to a method of use of such phosphorescent compound as a label or marker for binding with immunoglobulins or chemical analytes. It specifically relates to palladium (II) octaethylporphine alpha-isothiocyanate as a novel phosphorescent compound.

2. Description of the related art

Generally, the assays of the art have included radioimmunoassays for insulin and other hormones. The radioisotopes attach to hormones which have been chemically modified and then mixed with non-radioisotope labeled hormone. This admixed solution is contacted with a limited amount of antibody which is specific for the hormone. After separating the bound antibody from the unbound a determination can be made as to the concentration of the hormone in the patient's blood by comparing the radioactivity level of the patient's hormone to the radioactivities of known concentrations of hormones.

In other areas of the art, biological assays have provided a valuable tool in the evaluation of the effect of pharmacologically active compounds including biologically active proteins. Procedures developed for the bioassay of these types are usually biphasic. One procedure incubates the substrate cell population with the substance to be tested. The art has developed widely divergent procedures to carry out the quantitative analysis of the cellular response to the sample compound.

To obtain the quantitative analysis the art includes immunomediated assays which are quantitative only for the binding of the molecule to the cell. Another type of assay requires cell staining and visual or microscopic observation of a change in cellular morphology. Such assays are dependent on a subjective evaluation of the results.

The use of radioactive metabolites to determine viability of an antibody is less subjective than the colorimetric systems but the processing of numerous samples is time consuming, labor intensive and expensive. Further, counting of assay cell with the aid of an electronic particle counter to determine cell growth requires large multiples of each sample for accurate results and does not truly reflect the viability of the assay cells.

Even more recently, the art has developed colorimetric analysis of cell growth either by direct staining of the cell monolayer or by cellular dye uptake. For example, dye molecules have been used as labels for proteins (e.g. antibodies) to make reagents which have been associated with fluorescence readings. However, it is known in the art that labeling an antibody with a dye molecule and measuring the absorbance value does not provide a level of sensitivity sufficient to enable an accurate quantitative measurement of ligands in immunoassay systems.

Thus, the present state of the art indicates that although radioimmunoassays have been the cornerstone of modern immunoassay procedures, non-radioisotopic methods such as enzyme-linked immunosorbent assays and fluorescent immunoassays have become predominant in clinical laboratories due to aforementioned shortcomings of the radioimmunoassays and due to the licensing, special skills, expensive equipment, shipping and disposal problems associated with radioisotopes.

However, the present state of the art still has objections and has lack of sufficient sensitivity for immunoassay procedures to achieve full acceptability in the art. The non-radioisotope immunoassays generally lack the ability to detect molecular concentrations to the extent that radioimmunoassays can measure in large part due to the light scatter and other types of interference inherent in the testing procedure. Enzyme-linked immunosorbent assays require bulky, labile enzymes, are susceptible to inhibition and denaturation, and an additional incubation step is needed with a substrate to monitor the enzyme's activity.

It is recognized that fluorescence immunoassays achieve greater levels of sensitivity than enzyme-linked immunosorbent assays due to fluorescence molecules, i.e., the fluorophore labels, absorbing energy at one wavelength, i.e., excitation, and radiating energy at another wavelength, i.e., emission. This difference in wavelengths, known as the Stokes shift, can be used advantageously to gain sensitivity by having the excitation light project at 90° to the emission light being detected by a photomultiplier tube or other known detection devices. It is also recognized that each of the materials used as a fluorescent label has its own characteristics of required wavelength of excitation and resulting wavelength of fluorescent emission, i.e., has its own Stokes shift. If the label has a low Stokes shift, it is difficult and expensive to design light sensors which will respond to the wavelength of fluorescence and be relatively insensitive to the wavelength of the excitation light. Such sensors, as mentioned, use expensive defraction gratings inserted between the sample containing the fluorescent labels and the optical sensor. These are placed so that they are orthogonal to the direction of a beam of light at the excitation wavelength. There is still some background scatter and noise to contend with due to soluble molecules, small colloidal particles, or the presence of solid-phase material.

Thus, there is a need for a better luminescent compound for use in immunoassays, but the prior art considered as a whole, neither teaches nor suggests how the prior art compounds, if any, might be improved.

SUMMARY OF THE INVENTION

Accordingly, it is an object of this invention to provide a luminescent compound which has high selectivity as used in immunoassays.

It is a further object of this invention to provide an improved immunoassay system utilizing a novel luminescent compound having a relatively long Stokes shift.

It is a still further object of this invention to provide a immunoassay method utilizing a novel luminescent compound as a label or marker for binding with immunoglobulins or chemical analytes.

It is another object of the invention to provide a method for preparation of such novel luminescent compound.

It is therefore an object of the present invention to provide a sensitive phosphorescent label for immunoassays.

It is still another object of the present invention to provide a phosphorescent antibody comprising an antibody specific to an antigen to be detected, and conjugated to said antibody, a novel phosphorescent compound as a label.

Additional objects, advantages and novel features of the invention will be set forth in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

According to the present invention, the foregoing and other objects and advantages are attained by the production and recovery of a novel compound of the formula

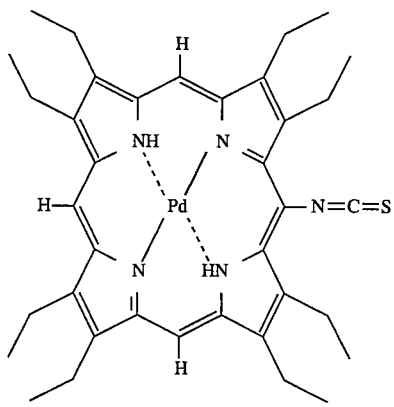

an example of which is palladium (II) octaethylporphine alpha-isothiocyanate.

In accordance with another aspect of the invention a phosphorescent labeled reagent is provided comprising antibodies, antigens, hormones, virus particles, haptens, bacterial components, drugs, monoclonal antibodies, anti-antibodies, immunoglobulins or proteins.

Another and further embodiment of this invention is a method for the preparation of a reagent useful for the detection of a ligand in a biological fluid, said reagent comprising an antibody to said ligand bound to the compound palladium (II) octaethylporphine alpha-isothiocyanate, comprising adding palladium (II) octaethylporphine alpha-isothiocyanate to a serum solution of immunoglobulin specific for the analyte of interest and incubating the admixture under conditions sufficient to enable said antibody to bind to the palladium (II) octaethylporphine alpha-isothiocyanate thereby forming said reagent.

A still further aspect of this invention is a phosphorescent antibody comprising an antibody specific to an antigen to be detected, and conjugated to said antibody, a phosphorescent compound of the formula

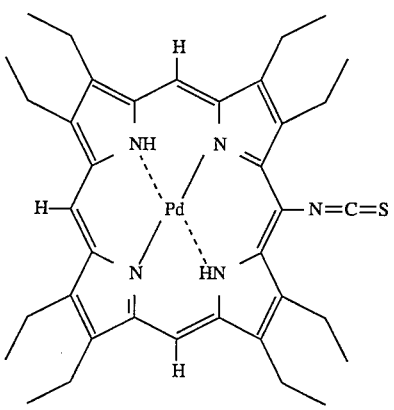

Another and particular embodiment of the invention is a method of preparing a phosphorescent compound which comprises the following protocol in sequence:

(a) preparing and recovering as a first sub-product of the formula

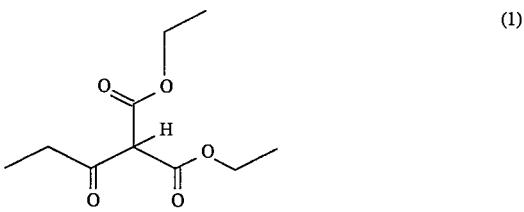

(1)

(b) transforming the first sub-product into a second sub-product of the formula

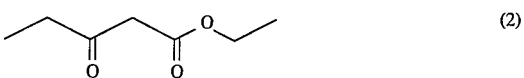

(2)

(c) producing from the second sub-product a third sub-product of the formula

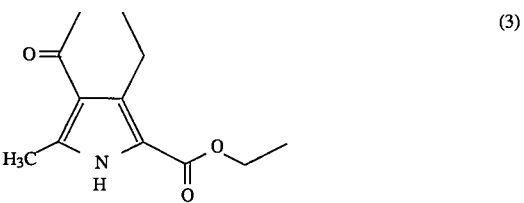

(3)

(d) producing from the third sub-product a fourth sub-product of the formula

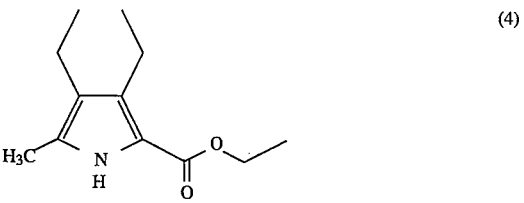

(4)

(e) producing from the fourth sub-product a fifth sub-product of the formula

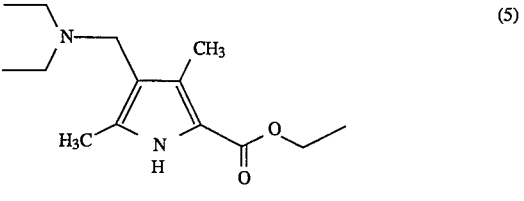

(5)

(f) producing from the fifth sub-product a sixth sub-product of the formula (g) producing from the sixth sub-product a seventh sub-product of the formula

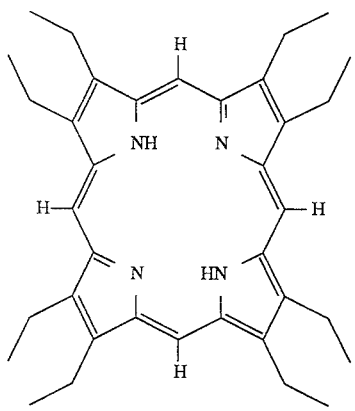
(6)

(h) producing from the seventh sub-product an eighth sub-product of the formula

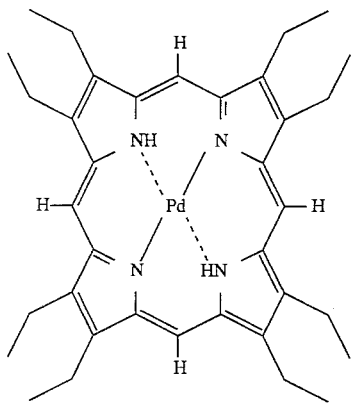
(7)

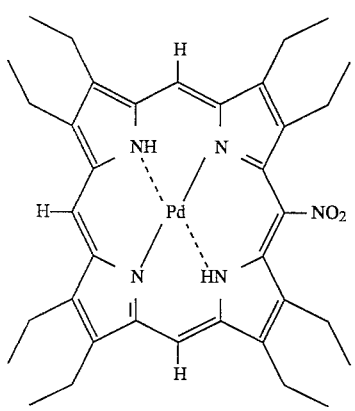
(8)

(i) producing from the eights sub-product a ninth sub-product of the formula and (j) producing from the ninth sub-product the phosphorescent compound of the formula

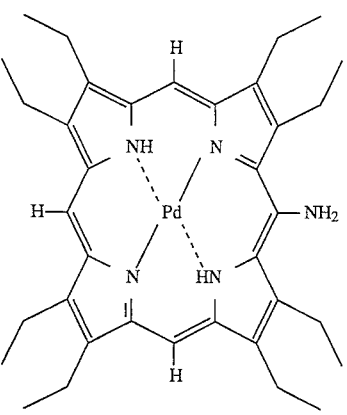
(9)

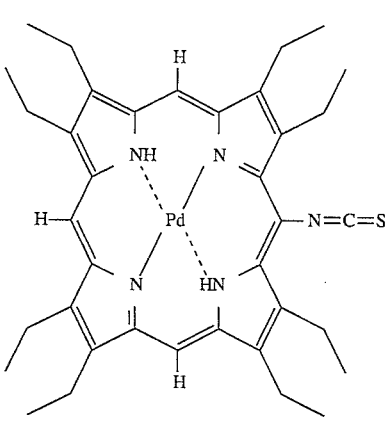
(10)

which is recovered.

BRIEF DESCRIPTION OF THE DRAWINGS

The advantages of the invention may be illustrated by reference to the drawings in which.

DESCRIPTION OF THE PREFERRED EMBODIMENT

Figure 1:
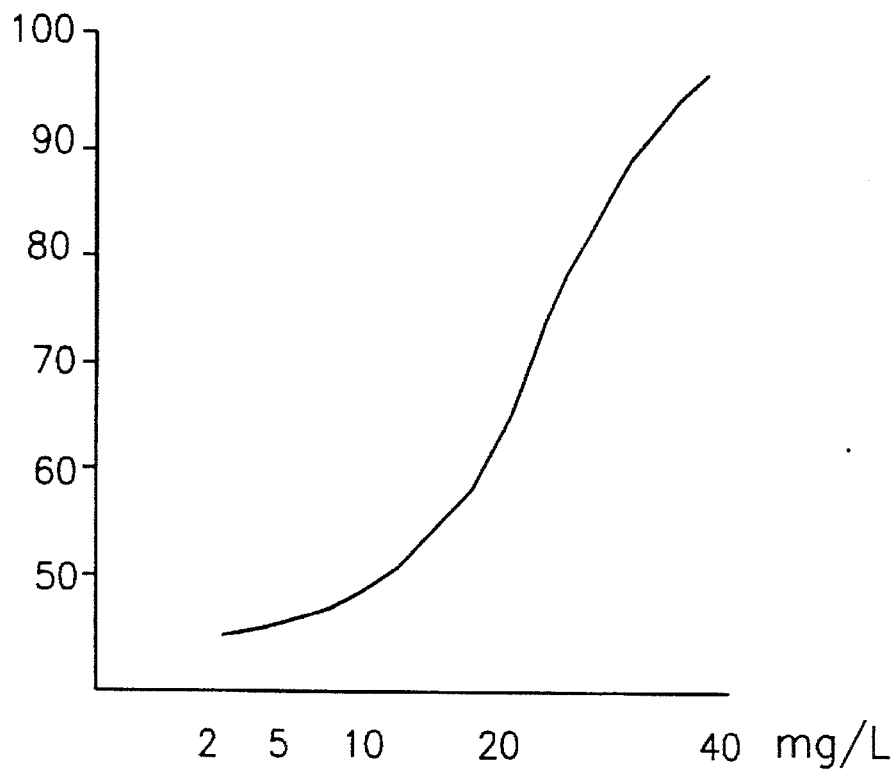
FIG. 1 illustrates the standard dose-response curve obtained of phosphorescence versus calibrators of carbamazepine.

In carrying out the present invention, phosphorescent immunoassays that employ the novel palladium compound as its label or marker have the same high degree of sensitivity as the radioimmunoassays but without the disadvantages of working with radioisotopes. This achieved high level of sensitivity is due to the fact that unlike the other non-isotopic methods, there is virtually no light scattering which produces a much greater signal-to-noise ratio. The practice of this invention achieves significance for determining the presence of infectious agents such as viral particles and microorganisms or for measuring hormones and other biochemical compounds that may be circulating in the blood in picograms per milliliter, or less, concentrations.

Luminescent molecules are capable of absorbing energy and emitting it as photons- The absorbed energy or light excites the electronic field of the molecule from its ground state singlet to a higher electronic state. The excited state may be detected by non-radiative conversion, such as heat, by radioactive transition directly to the ground state or through a semistable triplet state of phosphorence- This difference or loss of energy between the wavelength of excitation and the wavelength of emission is measured or determined as the Stokes shift. In fluorescent organic molecules, the Stokes shift typically is about 30 to 50 nanometers. In phosphorescent compounds the Stokes shift is considerably longer and may range from 150 nanometers to over 200 nanometers- The phosphorescent compound of this invention has a Stokes shift of not less than 150 nanometers, and typically may range from 200 to 300 nanometers.

Thus, an assay reagent of this invention is labeled with a phosphorescent labeling compound having a Stokes shift of not less than 150 nanometers to provide a labeled assay reagent- A labeled assay reagent is obtained by conjugating the reagent with a labeling agenn or compound. The preferred labeling agent or compound of this invention is the new palladium (II) octaethylporphine alpha-isothiocyanate. This new palladium labeling agent is preferably prepared by the method of this invention as more fully described hereinbelow.

The present invention is applicable to almost all assay reagents generally used by the art and which are capable of conjugation with the inventive palladium label. Some of the assay reagents which may be used with this invention include antibodies, antigens, hormones, virus particles, haptens, bacterial components, drugs, monoclonal antibodies, anti-antibodies, immunoglobulins and proteins. Examples of such assay reagents which are useful for the practice of this invention include thyroxin, triidothyronine, thyroid stimulating hormone, thyroxin binding giobulin, thyrotropin releasing hormone, digoxin, Gentamicin, Tobramycin, Phenytoin, Theophylline, Tetracycline, Hepatitis B surface antigen, Hepatitis B core antigen, Hepatitis A antigen, Carcinoembryonic antigen, Prostatic acid phosphatase and Human chorionic gonadotropin.

As mentioned, phosphorescence differs markedly from fluorescence in electronic energy levels and transitions. More particularly, in phosphorescence the absorbed energy or light also excites the electronic field of the molecule from ground state singlet to higher electronic states, but instead of returning directly to the ground state level, the phosphorescent molecule undergoes an intersystem crossing to a triplet state and then to the ground level state. while in the triplet state, there is a time delay from the time of excitation of the molecule to the phosphorescent emission from microseconds to several seconds. Therefore, by controlling the excitation light from the light source and the detection of the phosphorescence by means of a microprocessor in a computerized analytical system, precise measurements can be made and incorporated into biological, biochemical and clinical analyzers.

Heretofore, the art has been virtually unable to identify suitable phosphorescent labels that can be conjugated to immunoglobulins or to antigenic substances or analytes. To be effective, the prior phosphorescent compounds must be kept at extremely low temperature, e.g. minus 20° C., and must be carefully maintained at a predetermined pH level. In short, phosphorescent compounds are very sensitive to changes in environment. Even minor changes in pH, polarity, oxidation state, or the presence of quenching groups can significantly alter phosphorescent yields or significantly shift wavelengths. Even the presence of two phosphorescent probes in a protein can cause self-quenching if absorption and emission wavelengths overlap.

The new compound of this invention, palladium (II) octaethylporphine alpha-isothiocyanate, does not exhibit the aforementioned limitations and, therefore, offers a major advance in the development of more sensitive diagnostic immunoassays.

The invention will be further described and clarified by a consideration of the following detailed examples, which are intended to be purely exemplary of the use of the invention.

PROTOCOL FOR THE SYNTHESIS OF PALLADIUM (II) OCTAETHYLPORPHINE ALPHA-ISOTHIOCYANATE:

1. Preparation of Diethyl Propionylmalonate

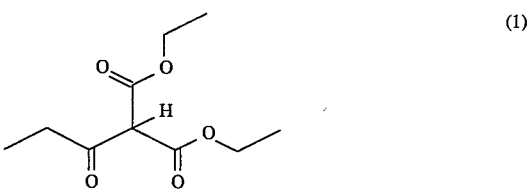

(1)

A Grignard reagent is prepared by adding 300 grams, 12.34 moles, of magnesium turnings (Aldrich Chemical Company, Milwaukee, WI, catalog number 20,090-5) into a 12 liter round-bottom flask equipped with a magnetic stirring bar, addition funnel, gas inlet (nitrogen), and condenser. Absolute ethanol (300 mL, Aldrich A24,511-9) is added to the flask. In a separate flask prepare a mixture of diethyl malonate (1920 g, 12 mol, Aldrich D9,775-4) and 960 mL of absolute ethanol. Pour approximately 300 mL of the diethyl malonate solution into the reaction flask containing the magnesium turnings. Start a slow stream of nitrogen through the solution. Add 5.0 mL of carbon tetrachloride (Aldrich 27,065-2) to the reaction flask to initiate the Grignard reaction. Stirring is begun when the exothermic reaction becomes vigorous. Cautiously add the remaining diethyl malonate solution to the reaction vessel and reflux under steam until the mixture becomes too thick to stir. Cool the mixture to room temperature and add absolute ether (3200 mL, Aldrich 17,926-4). Reflux with steam until only a few traces of magnesium remain. Allow the mixture to cool below 65 degrees Celsius and add freshly distilled propionyl chloride (1110 g, 12 mol, Aldrich P5,155-9) slowly to the reaction mixture. Cover the flask and leave undisturbed for 18 hours at room temperature. Prepare a sulfuric acid solution from 588 g of sulfuric acid (6 mol, Aldrich 25,810-5) poured onto excess crushed ice and diluted to 3500 mL with deionized water. The cold sulfuric acid solution is added to the stirred reaction mixture dropwise at a slow rate. The mixture is separated and the organic layer is thoroughly washed with deionized water. The solvent is then removed and the remaining oil is distilled under vacuum at 20 mm Hg with the fraction boiling at 123 to 140 degrees Celsius, at 20 mm Hg, collected. The expected yield is about 2000 grams.

2. Preparation of Ethyl propionylacetate

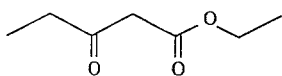 (2)

A stirred mixture of 1.0 kg of diethyl propionylmalonate and 2.0 liters of deionized water is slowly distilled at atmospheric pressure for 4.5 hours. Additional water is occasionally added to replace any that has distilled over. After cooling, the distillate is combined with the residue. The mixture is separated and the aqueous phase extracted twice with ether. The organic layers are combined and solvent removed with steam. The remaining oil is then distilled at 26 mm Hg with the fraction boiling at 90 to 115 degrees Celsius collected. The expected yield is about 535 grams.

3. Preparation of 4-Acetyl-2-ethoxycarbonyl-3-ethyl-5methylpyrrole

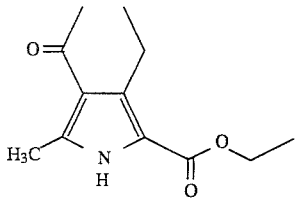 (3)

Add 148 grams of the crude ethyl propionylacetate along with 200 mL of glacial acetic acid (Aldrich 24,285-3) into an ice-cooled Erlenmayer flask equipped with a magnetic stirrer. A solution of sodium nitrite (69 grams, Aldrich 23,721-3) in 110 mL of deionized water is added dropwise to the above solution at such a rate as to maintain the temperature below 45 degrees Celsius. Into a 2000 mL three-necked round bottom flask equipped with a magnetic stirring bar, addition funnel, condenser, and nitrogen inlet add a solution of 2,4-pentanedione (150 mL, 1.5 mol, Aldrich P775-4) and glacial acetic acid (200 mL). Add the ethyl oximinopropionyl acetate solution obtained from above dropwise into the reaction vessel along with zinc dust (260 grams, 4 mol, Aldrich 20,998-8) in a deionized water slurry at such a rate as to maintain the temperature close to reflux. Halfway through the addition add an additional 50 mL of 2,4-pentanedione and 200 mL of glacial acetic acid. Before the temperature has dropped below 100 degrees Celsius the solution is decanted and the residual zinc is washed with acetic acid. The combined supernatant and washings are diluted four times their volume with water. The product will oil out and crystallize. The crystals are then washed with deionized water and allowed to dry. The solid is the dissolved with methylene dichloride (Aldrich 27,056-3) and the organic phase separated and washed with deionized water. The methylene dichloride is removed by steam until only a small amount remains. Hot hexane is added and the solution is distilled until a small amount is left covering the solid. Filter, wash with room temperature hexane, and air dry. Expected yield is about 120 grams. Repeat until about 1 kilogram is available.

4. Preparation of 2-Ethoxycarbonyl-3,4-diethyl-5methyl pyrrole.

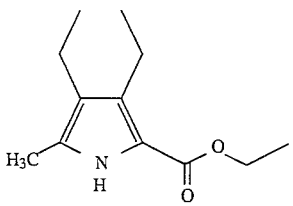 (4)

Into an ice-cooled 12 liter round-bottom flask equipped with a magnetic stirrer, additional funnel, nitrogen inlet, and condenser is placed (under nitrogen) 1000 grams of the crude 4-acetyl-2-ethoxycarbonyl-3-ethyl-5-methylpyrrole from the previous step. Tetrahydrofuran (5500 mL, Aldrich 27,038-5) is added and the mixture is stirred until the solid is dissolved. Sodium borohydride (312 grams, 8 mol, Aldrich 21,346-2) is added to the chilled solution, followed by dropwise addition of boron trifluoride etherate (1600 grams, Aldrich 17,550-1). The drops should be slow enough to maintain temperature at 10 degrees Celsius. The mixture is then stirred for an additional hour. Excess glacial acetic acid is cautiously added until gas evolution has ceased, after which excess deionized water is added. The aqueous phase is separated and organic phase filtered to remove boric acid and then washed with ether. The combined tetrahydrofuran/ether solution is taken down to dryness and the residue dissolved in 95% ethanol (2000 mL, Aldrich 24,511-9). Diethylamine (250 mL, Aldrich 11,000-0) and 37% aqueous formaldehyde (250 mL, Aldrich 25,254-9) are added, followed by concentrated HCl (5 mL, Aldrich 25,814-8). The mixture is refluxed 18 hours, taken down to dryness, and the residue dissolved in ether. The ethereal solution is extracted with deionized water, and then with 5% HCl until the washings remain acidic. The solution is given a final wash with water and the volume is reduced to 1500 mL. The product will crystallize upon cooling. To this mixture add 70% aqueous methanol (200 mL, Aldrich 27,04704). Filter the resulting slurry and wash the product with 70% methanol. Air dry. The expected yield is about 740 grams.

5. Preparation of 5-N,N-Diethylaminomethyl-2-ethoxycarbonyl-3,4-diethylpyrrole

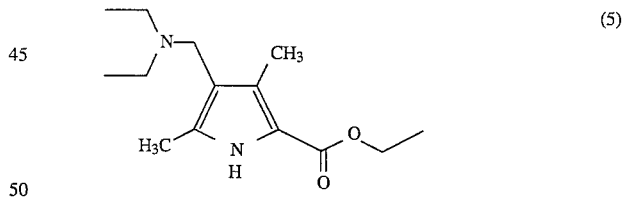 (5)

To an uncooled stirred solution of dry 2-ethoxycarbonyl-3,4-diethyl-5-methylpyrrole from the previous step (104.5 grams, 0.5 mol) in anhydrous ether (1500 mL, Aldrich 17,926-4), under nitrogen, is added dropwise and rapidly, a solution of bromine (83 grams, 0.52 mol, Aldrich 27,757-6) in dichloromethane (270 mL, Aldrich 27,056-3). Reflux with steam. Use caution as the reaction is exothermic. After 20 minutes the addition is complete. Stir for an additional 20 minutes. Diethylamine (175 mL, Aldrich 32,027-7) is added to the rapidly stirred solution over a period of 5 minutes causing the mixture to reflux and change from deep red to pale yellow. Stir for an additional 30 minutes. Deionized water (1000 mL) is added and the mixture is separated. The organic phase is washed with deionized water and then excess crushed ice is added. The water is separated and 37% HCl (100 mL, Aldrich 25,814-8) is diluted to 1000 mL with ice and water and used to wash the organic phase. The aqueous phase is then quickly washed with ether and added to 30% ammonium hydroxide (100 mL, Aldrich 22-122-8) in deionized water (100 mL). The product, which should immediately oil out, is extracted from the aqueous phase with petroleum ether (300 mL, Aldrich 26,173-4). The organic layer is washed with deionized water, dried over sodium sulfate, filtered, and the solvent removed under vacuum. The expected yield is about 135 grams.

6. Preparation of Octaethylporphyrin

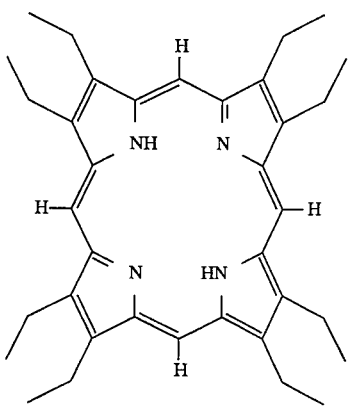
(6)

The previously prepared compound (28.0 g, 0.1 mol) is added to 100 mL of 95% ethanol (Aldrich 24,511-9) and treated with a solution of potassium hydroxide (13.2 grams, 0.2 mol, Aldrich 22,147-3) and 20 mL of deionized water. The mixture is heated on a steam bath for 3 hours and then diluted to 200 mL with deionized water. The mixture is then cooled in an ice bath and 200 mL of glacial acetic acid is added. The mixture is then boiled with stirring. When the solution becomes dark, air is bubbled through it. After boiling for 1 hour, by which time the solution is reduced to half its original volume, the solution is diluted with an equal volume of methanol (Aldrich 27,047-4). After cooling to room temperature, the product is collected by filtration and washed with methanol to give crystals of octaethylporphyrin. The expected yield is about 7 grams. The octaethylporphyrin can be further recrystallized from toluene. Melting point of the crystals should be sharp at approximately 324 degrees Celsius. (See Paine, John B. III et al., "An Improved Synthesis of Octaethylporphyrinp", J Org Chem, Vol 41, No 24, 1976 (3857–3860) for further details and which is incorporated herein by reference thereto.)

7. Preparation of Palladium (II) Octaethylporphyrin

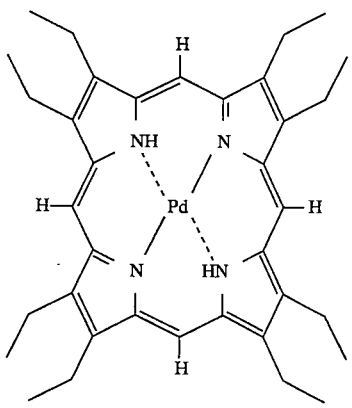
(7)

Octaethylporphyrin (100 mg), palladium chloride (1 g, Aldrich 20,588-5), and sodium acetate (1g, Aldrich 24,124-5) are heated under reflux in glacial acetic acid (100 mL) for 30 minutes. A sample is taken, diluted with chloroform, and checked for a band around 620 nm on a UV/VIS spectrophotometer. If the test is negative, the solution is evaporated to a volume of approximately 30 to 40 mL, refluxed again for 10 minutes, then left at room temperature overnight. Crystals are formed, filtered, and recrystallized from glacial acetic acid. The expected yield is about 90 mg. (Reference: Fuhrhop, J. H. and K. M. Smith, "Laboratory Methods", Chapter 19 in porphyrins and Metalloporphyrins, Kevin M. Smith, editor, Elsevier Scientific Publishing Company, Amsterdam, 1975, page 797, which is incorporated herein by reference thereto.)

8. Preparation of Meso-Nitro-Palladium Octaethylporphyrin

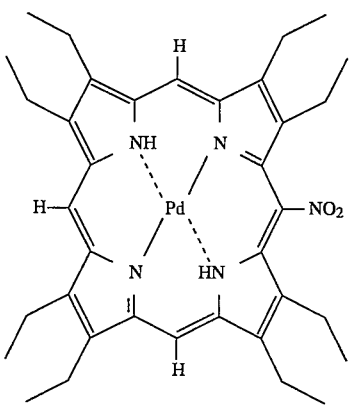
(8)

Palladium Octaethylporphyrin (200 mg from repeated synthesis of previous step, 0.3 mol) is treated with an ice-cold mixture of fuming nitric acid (32 mL, Aldrich 25,812-1) and glacial acetic acid (32 mL). The mixture is shaken for 90 seconds and poured into ice water. Ether is added to extract the product and high performance liquid chromatography to further isolate and purify the compound. Crystallization from benzene yields about 160 mg of red-brown needles. The melting point is approximately 250 degrees Celsius. (Reference: Fuhrhop, cited above, page 818)

9. Preparation of Meso-Amino-Palladium Octaethylporphyrin

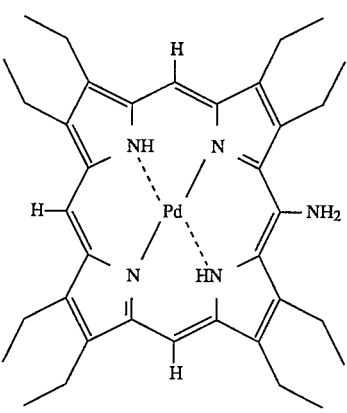
(9)

The above nitro product is scaled up until about 8 grams are available, then 7.6 g (0,011 mol) is added with Raney nickel (1.0 g, Aldrich 22,167-8) in absolute ethanol (200 mL) in a round-bottom flask and heated under 50 pounds pressure with a heat lamp until hydrogen ceases to be taken up. The solution is evaporated to a volume of about 30 mL and the residue poured into a 1 liter ice water solution.

Crystals are collected, washed with water, and dried. Expected yield is about 6 grams. (See Riggs, J. L., et al, "Isothiocyanate Compounds as Fluorescent Labeling Agents for Immune Serum", Am J Path, Vol 34, 1958, pages 1081-97 for further information and which is incorporated herein by reference thereto.)

10. Preparation of Palladium (II) Octaethylporphine alpha-Isothiocyanate

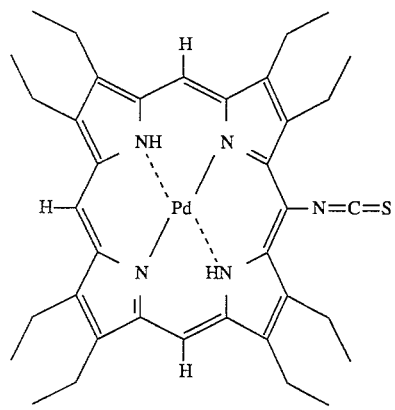

(10)

Five grams of the amine product obtained in step 9 (7.6 mmol) in acetone (20 mL, Aldrich 27,072-5) is added dropwise to stirred solution of 4 mL of thiophosgene (Aldrich 11,515-0) in 20 mL of acetone at 40 degrees Celsius. The solution is heated at reflux temperature for 4 hours and the solvent and excess thiophosgene removed under reduced pressure. The residue is dissolved in acetone (20 mL) and the solution is added dropwise to petroleum ether (1200 mL). The precipitated solid is collected by filtration, washed with petroleum ether, and dried, The expected yield is about 4.5 grams. (Refer to Riggs, cited previously).

11. Preparation of Palladium (II) Octaethylprophine alpha-Isothiocyanate Labeled Antibody.

To a 1.0 mL serum solution containing approximately 20 mg/ml of immunoglobulin specific for the analyte of interest add 0.2 mg Palladium (II) Octaethylporphine alphaIsothiocyanate (herein after referred to as PdOEPITC) dissolved in 100 microliters of acetone to 5.0 mL of sodium carbonate-bicarbonate buffer (0.5 M with pH adjusted to 9.5). Dilute to 50 mL with normal physiologic saline and incubate for 4 hours at 8 degrees Celsius. Separate the labeled antibody from unlabeled by gel filtration on SEPHADEX G-25 (SIGMA CHEMICAL COMPANY G 25) and DEAE-cellulose in 0.1M NaCl containing 0.005M phosphate buffer (pH 7.2). Fractions are collected and pooled until the molar ratio is approximately 1:2 PdOEPITC to antibody, based on a molar absorptivity of approximately 163,500 L/mole per cm at 399 nm. (Refer to Kawamura, A., "Preparation of Labeled Antibody" in *Fluorescent Antibody Techniques and Their Applications,* Univ. of Tokyo Press, 1977, pages 37–66, which is incorporated herein by reference thereto.)

EXAMPLES

PHOSPHORESCENT IMMUNOASSAY FOR CARBAMAZEPINE

Preparation of Carbamazepine Calibrators:

A 1 gram/liter stock solution of the anticonvulsant compound carbamazepine (Aldrich 30,948-6), more commonly known as Tegretol™, which is a trade marked brand of Geigy Pharmaceuticals division of Ciba-Geigy Corporation, was prepared in ethanol. Calibrators for determining a standard dose-response curve were prepared by adding the stock solution to normal human serum to give concentrations of 2, 5, 10, 20, and 40 mg/L.

Preparation of Phosphorescent labeled Carbamazepine:

PdOEPITC (12 mg) was reacted with 3 mg of carbamazepine in 800 microliters of dimethylformamide (Aldrich 27,054-7) containing 10 mL of triethylamine (Aldrich 23,962-3) per liter of dimethylformamide. The reaction was allowed to continue for 18 hours at room temperature. A 250 microliter aliquot was then applied to a silica gel plate for a preparative thin-layer chromatography extraction. The developer was a mixture of chloroform, methanol, and glacial acetic acid (70/25/5 percent by volume) that separated out a major component which was then scraped from the plate and eluted into 3 mL of ethanol. The concentration of PdOEPITC-Carbamazepine was estimated by using the molar absorptivity of $5.8 \times 10^4$ l/mol/cm (see Mercer-Smith, J Am Chem Soc 100:9 (1978) for additional information on absorptivities of palladium octaethylporphyrin compounds).

Phosphorescent Immunoassay Procedure:

Assays are performed in duplicate to 20° to 25° Celsius. To 5 microliters of serum calibrators or sample specimen add 100 microliters of PdOEPITC-Carbamazepine and 100 microliters of antiserum (Sigma Chemical Company, C8795) diluted five-fold into quartz spectrophotometer cuvets. Add 1.3 milliliters of diluent buffer containing 100 mmol/L sodium phosphate, 5 g/L bovine albumin, 3 g/L sodium azide, and 12 g/L sodium sulfite, which acts as a deoxygenator (see Sidki, Ahmed M., et al., Clin. Chem. 32/1, 53–56 (1986). Incubate for 10 minutes and measure the relative phosphorescence. The standard dose-response curve (FIG. 1) depicts the results obtained of phosphorescence versus calibrators of carbamazepine. Phosphorescence measurements were made on a Perkin-Elmer, Norwalk, Connecticut, Model LS-5 luminescence spectrometer. The excitation wavelength was set for 323 nanometers and emission detected at 662 nanometers.

PHOSPHORESCENT IMMUNOASSAY FOR DIGOXIN

Preparation of Digoxin Calibrators:

Ten milligrams of crystalline digoxin (Sigma, D6003) was dissolved in 50 milliliters of 95% ethanol and diluted with 10 mmol/liter Tris (hydroxymethyl) aminomethane saline buffer (Sigma 850-4), pH 7.4, to final concentrations of 0.2, 0.5, 1.0, 2.0, 3.0, 5.0, and 10.0 nanograms/milliliter.

Preparation of Phosphorescent Labeled Anti-Digoxin:

Dissolve 5 milligrams of PdOEPITC in 5 milliliters of acetone by stirring in a calibrated weighing bottle. Store stock solution at 4° Celsius. Two milliliters of monoclonal anti-digoxin (Sigma D8156) that has a minimum titer of 1:50,000 is cooled at 0° Celsius in an ice bath while stirring and brought to a pH of 9.0 to 9.5 by addition of 0.1 N NaOH. The anti-digoxin solution is added dropwise to 0.1 milliliters of the stock solution of PdOEPITC and the mixture stirred in an ice bath for one hour. The pH is maintained at 9.0 to 9.6 by addition of 0.05M sodium carbonate or bicarbonate. Incubate the mixture for 3.5 hours, while stirring, at 4° Celsius. Centrifuge the mixture for 10 minutes at 1000×g at 4° Celsius. Decant, discarding the precipitate. The reaction mixture is applied to a column (3 ×30 cm) of SEPHADEX G-50 (Sigma G50–150) equilibrated with 0.05M NaCl in 0.01M phosphate buffer. Elution is performed with the same buffer. Eluates containing the first peak (conjugated immunoglobulin) are collected and pooled. The pooled eluates are applied to a column (2×21 cm) of DEAE-cellulose (Sigma D8257) equilibrated with 0.05M NaCl in 0.01M sodium phosphate buffer, pH 7.5. Stepwise elution is performed with solutions of increasing NaCl concentration (0.05, 0.1, 0.2, and 0.3M) in the same buffer. The eluate is then stored at 4° Celsius until needed.

Figure 2:
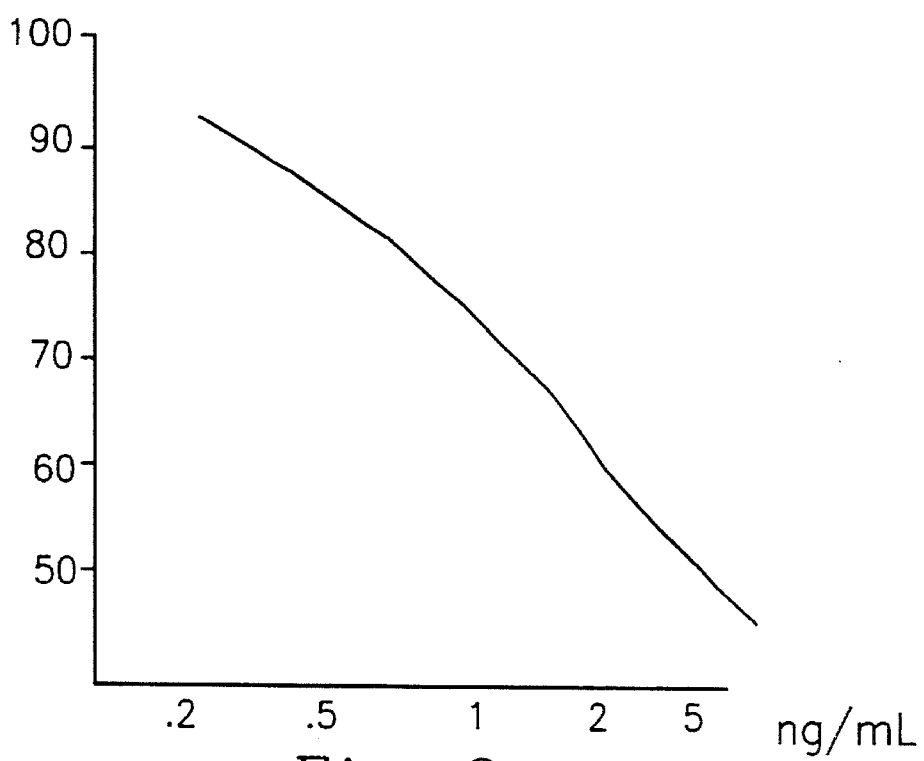
FIG. 2 illustrates the standard dose-response curve of phosphorescence versus calibrators of digoxin.

Phosphorescent Immunoassay Procedure:

Assays are performed in duplicate at 20° to 25° Celsius. To 5 microliters of serum calibrators or sample specimen add 100 microliters of anti-digoxin conjugated PdOEPITC to a quartz cuvet. Add 1.3 milliliters of diluent buffer containing 100 mmol/L sodium phosphate, 5 g/L bovine albumin, 3 g/L sodium azide, and 12 g/L sodium sulfite. Incubate for 10 minutes and measure the relative phosphorescence. The standard dose-response curve (FIG. 2) illustrates the phosphorescence versus calibrators of digoxin. As in the previous example, measurements were made on a Perkin-Elmer Model LS-5 luminescence spectrometer. The excitation was set for 323 nanometers and emission detected at 662 nanometers.

The invention is clearly new and useful. Moreover, it is not obvious to those of ordinary skill in the art at the time the invention was made, in view of the state of the prior art when considered as a whole in accordance with the requirements of law.

This invention pioneers the art of phosphorescent labels for immunoassays. Accordingly, the claims that follow are entitled to broad interpretation so as to protect from piracy the heart or essence of this breakthrough invention.

It is also to be understood that the following claims are intended to cover all of the generic and specific features of the invention herein described, and all statements of the scope of the invention, as a matter of language, might be said to fall therebetween.

NOW, that the invention has been fully described,

What is claimed is:

1. A phosphorescent labeled compound comprising a specific binding partner conjugated to a palladium (II) ochaethylporphine alpha-isothiocyanate label, said label having a Stokes shift of not less than 150 nanometers.

2. The phosphorescent labeled compound of claim 1 wherein the specific binding partner is an antigen, an antibody, or a hapten.

3. The phosphorescent labeled compound of claim 1 wherein the specific binding partner is a viral or bacterial antigen.

4. The phosphorescent labeled compound of claim 1 wherein the specific binding partner is a protein, a drug or a hormone.

5. The phosphorescent labeled compound of claim 1 wherein the label has a Stokes shift of from 200 to 300 nanometers.

6. A method of preparing a phosphorescent labeled compound which comprises:

(a) forming a mixture of (i) a palladium (II) octaethylporphine alpha-isothiocyanate having a Stokes shift of not less than 150 nanometers and (ii) a specific binding partner; and, (b) incubating the mixture under conditions sufficient to covalently conjugate the specific binding partner to the palladium (II) octaethylporphine alpha-isothiocyanate through an isothiocyanate moiety on the palladium (II) octaethylporphine alpha-isothiocyanate, thereby forming the phophorescent labeled compound.

7. The method of claim 6 wherein the palladium (II) octaethylporphine alpha-thiocyanate has a Stokes shift from 200 to 300 nanometers.

* * * * *